United States Patent [19]

Bojsen et al.

[11] Patent Number: 5,767,378

[45] Date of Patent: Jun. 16, 1998

[54] MANNOSE OR XYLOSE BASED POSITIVE SELECTION

[75] Inventors: Kirsten Bojsen, Alleroed, Denmark; Iain Donaldson, Abingdon, United Kingdom; Anna Haldrup, Soborg, Denmark; Morten Joersboe, Nykoebing Falster, Denmark; Jette Dina Kreiberg, Roskilde, Denmark; John Nielsen, Copenhagen K, Denmark; Finn Thyge Okkels, Roskilde, Denmark; Steen Guldager Petersen, Rodovre, Denmark

[73] Assignee: Novartis AG

[21] Appl. No.: 505,302

[22] PCT Filed: Feb. 28, 1994

[86] PCT No.: PCT/EP94/00575

§ 371 Date: Oct. 3, 1995

§ 102(e) Date: Oct. 3, 1995

[87] PCT Pub. No.: WO94/20627

PCT Pub. Date: Sep. 15, 1994

[30] Foreign Application Priority Data

Mar. 2, 1993 [GB] United Kingdom ............... 9304200

[51] Int. Cl.[6] .............. C12N 15/29; C12N 15/82; C12N 15/31; A01H 5/00
[52] U.S. Cl. ............... 800/205; 800/DIG. 40; 800/DIG. 42; 800/DIG. 56; 435/172.3; 435/240.4; 435/233; 435/194; 536/23.2; 536/23.7
[58] Field of Search ............... 800/205, DIG. 40, 800/DIG. 56, DIG. 42; 435/240.4, 172.3, 320.1, 233, 194; 536/23.7, 23.2

[56] References Cited

U.S. PATENT DOCUMENTS 4,857,467 8/1989 Sreekrishna et al. ............... 435/255

OTHER PUBLICATIONS

Napoli et al. Introduction of a Chimeric Chalcone Synthase Gene into Petunia Results in Reversible Co-Suppression of Homologous Genes in trans. The Plant Cell, vol. 2, 279–289, Apr. 1990.

Piruzyan et al. *E. coli* glucose isomerase gene expression in transgenic plants. Chemical Abstracts, vol. 110 No. 25, p. 173 abstracts No. 226554, 1989.

Mjles et al. Nucleotide Sequence and transcriptional start point of the phosphomannose isomerase gene of *E. coli*. Gene, 32 (1984), 41–48.

Posno et al. Complementation of the Inability of Lactobacillus Strains To Utilize D–Xylose Catabolism–Encoding Genes of *Lactobacillus pentosus*. Applied and Environmental Microbiology, pp. 2764–2766, Sep. 1991.

Watkins et al. Inhibition of Pear Fruit Ripening by Mannose. Plant Physiol. (1987) 85, 56–61.

Smith et al. Antisense RNA inhibition of polygalcturonase gene expression in transgenic tomatoes. Natur vol. 334, pp. 724–726, 25 Aug. 1988.

*Primary Examiner*—Douglas W. Robinson
*Assistant Examiner*—Thomas Haas
*Attorney, Agent, or Firm*—Lynn Marcus-Wyner Thomas Hoxie

[57] ABSTRACT

The present invention provides a method for identifying or selecting from a population of eukaryotic cells cultivated on or in a medium containing at least one compound, cells which have a metabolic advantage as a result of having been transformed, wherein:

i) the cells are transformed with a nucleotide sequence or a co-introduced nucleotide sequence one of which comprises a region which: (a) encodes a protein which is involved in the metabolism of the compound, and/or (b) regulates the activity of the protein; and ii) the compound is mannose or xylose or a derivative or a precursor of these, or a substrate of the protein, or is capable of being metabolized by the transformed cells into such a substrate, with the proviso that the compound is not mannose when the protein is mannose 6 phosphate isomerase.

The invention also includes a method according to the preceding paragraph wherein the compounds are not so limited with the proviso that an agent which reduces the toxicity to the cells of the compound is added to the medium. It is preferred that where a toxicity-reducing agent has been added to the culture medium, the compound is mannose and the nucleotide or co-introduced nucleotide sequence encodes mannose-6-phosphate isomerase.

18 Claims, 4 Drawing Sheets

Plasmid EPL

DW2t: CaMV terminator Pst-KpnI fragment isolated from the pDW2 plasmid.

Restriction sites:

E : Eco RI
C : Cla I
B : Bam HI
B/ Bc : Bam HI/ Bcl I, Bcl I ligated into Bam HI
H : Hind III
H II : Hinc II
H/Sm : Hind III*/ Sma I, filled in Hind III site blunt end ligated with Sma I K : Kpn I
P : Pst I
Sa : Sac I
S : Sal I
Se : Spe I
Sp : Sph I
X : Xba I ▨▨ ▨▨ : Promotor
■ : Terminator
▭ : Coding sequence
←→ : Direction unknown

MANNOSE OR XYLOSE BASED POSITIVE SELECTION

The present invention relates to a method for selecting genetically transformed cells into which a desired nucleotide sequence has been incorporated by providing the transformed cells with a selective advantage. The selective advantage possessed by the transformed cells may be due to their enhanced capacity, relative to non-transformed cells, to utilize an added compound as a nutrient, growth factor or energy source.

It is known that when genetic material is to be introduced into a population of cells by transformation, only a certain number of the cells are successfully transformed. Identification and separation of the transformed cells has traditionally been accomplished using "negative selection", whereby the transformed cells are able to survive and grow, while the non-transformed cells are subjected to growth inhibition or perhaps even killed by a substance which the transformed cells, by virtue of their transformation, are able to tolerate.

For example, when a population of plant cells is transformed, selection of the transformed cells typically relies on the presence in the transformed cells of a "selection gene" which provides for antibiotic or herbicide resistance. The selection gene—which in itself may have no useful function in the transformed plant (and may in fact be undesirable in the plant) is coupled to or co-introduced with the desired gene to be incorporated into the plant, so that both genes are incorporated into the population of cells, or rather into certain of the cells in the population, since it is difficult, if not impossible, in practice to transform all of the cells. The cells are then cultivated on or in a medium containing the antibiotic or herbicide to which the genetically transformed cells are resistant by virtue of the selection gene, thereby allowing the transformed cells to be identified, since the non-transformed cells which do not contain the antibiotic or herbicide resistance gene—are subjected to growth inhibition or are killed.

These negative selection methods have certain disadvantages. For example, the non-transformed cells may die because of the presence of antibiotics or herbicides in the growth medium. As a result, when the population of cells is a coherent tissue there is a risk that not only the non-transformed cells but also the transformed cells may die, due to the fact that the death of the non-transformed cells may cut off the supply of nutrients to the transformed cells or because the damaged or dying non-transformed cells may excrete toxic compounds.

Another disadvantage of negative selection is that the presence of an unnecessary gene, for example providing for antibiotic resistance, may be undesirable. There is concern among environmental groups and governmental authorities about whether it is safe to incorporate genes coding for antibiotic resistance into plants and microorganisms. This concern is of particular significance for food plants and for microorganisms which are not designed to be used in a closed environment (e.g. microorganisms for use in agriculture), as well as for microorganisms which are designed for use in a closed environment, but which may accidently be released therefrom.

A further disadvantage of negative selection is that plant tissues or cells treated with toxic substances become more susceptible to bacterial infection. This is a problem when Agrobacterium is used as a transformation vector, because the treated tissues or cells sometimes become overgrown with the bacteria even though antibiotics are used to prevent bacterial growth.

In addition, selection of cells or tissues using negative selection requires precise timing of expression of the introduced genes in relation to the selection process. If the transgenic cells are treated with a toxic compound before the detoxifying gene is expressed or before enough gene products are produced to ameliorate the action of the toxic compound, both the transgenic and the non-transgenic cells will be killed If selection is performed too late, the selection of transgenic cells or tissues may be hindered by, for example. shoot or callus formation from non-transgenic cells or tissues which forms a barrier to the penetration of the compound used to select the transformed cells.

The above disadvantages are overcome, at least to a substantial extent, by the method according to the present invention (termed "positive selection" or combined "positive/negative" selection) which makes it possible to identify and isolate genetically transformed cells without damaging or killing the non-transformed cells in the population and without co-introduction of antibiotic or herbicide resistance genes. In addition to the fact that the need for antibiotic or herbicide resistance genes is eliminated, the positive selection method according to the present invention is often far more efficient than traditional negative selection, and a combination of positive and negative selection gives a selection frequency of transgenic shoots as good as if not higher than that obtained using negative selection alone. Furthermore, the use of positive selection provides the advantage that a single gene may be used as both a reporter gene and a selection gene, resulting in simplification of vector constructions, more stable constructions and a 100% correlation between the expression of reporter and selection genes.

Positive selection may also eliminate the above-mentioned problems with regard to timing, since selective compounds may be produced as a consequence of the action of gene products, resulting from expression of the introduced gene, on particular substrates. Thus, the selective compound may accumulate as a consequence of expression of the selection gene, the selection effect appearing when a sufficient amount of the selective compound has been produced.

According to the present invention there is provided a method for identifying or selecting from a population of eukaryotic cells cultivated on or in a medium containing at least one compound, cells which have a metabolic advantage as a result of having being transformed, wherein:

i) the cells are transformed with a nucleotide sequence or a co-introduced nucleotide sequence one of which comprises a region which: (a) encodes a protein which is involved in the metabolism of the compound, and/or (b) regulates the activity of the gene encoding the protein; and ii) the compound is mannose or xylose or a derivative or a precursor of these, or a substrate of the protein, or is capable of being metabolized by the transformed cells into such a substrate, with the proviso that the compound is not mannose when the protein is mannose 6 phosphate isomerase.

The invention also includes a method for identifying or selecting from a population of eukaryotic cells cultivated on or in a medium containing at least one compound, cells which have a metabolic advantage as a result of having being transformed, wherein:

i) the cells are transformed with a nucleotide sequence or a co-introduced nucleotide sequence one of which comprises a region which: (a) encodes a protein which is involved in the metabolism of the compound, and/or (b) regulates the activity of the gene encoding the protein; and ii) an agent which reduces the toxicity to the cells of the compound is added to the medium.

It is preferred that where a toxicity reducing agent has been added to the culture medium, the compound is mannose and the nucleotide or co-introduced nucleotide sequence encodes mannose-6-phosphate isomerase.

Cells which have a "metabolic advantage" inter alia are able to grow more quickly than disadvantaged cells, and/or are advantageously able to utilize substrates (such as nutrient precursors etc.) which disadvantaged cells are not able to utilize, and/or are able to detoxify substrates which are toxic or otherwise growth inhibitory to disadvantaged cells.

A protein which is "involved in the metabolism of a compound" is typically, but not exclusively, an enzyme which may be responsible directly or indirectly for the production or utilization of the compound or its derivatives or precursors. The protein may also be involved in the metabolism of a compound if it binds to it, transfers it from one site to another within the cell or tissue or organism or otherwise sequesters it thereby altering its local availability.

A region of nucleotide sequence which "regulates the activity of a gene encoding a protein" may alter the level of expression of an endogenous gene by being a promoter, or having a promoter activity therefor, and by being introduced in or near its vicinity. By "near" is meant up to 10,000 kb. Alternatively, indirect regulation may arise by altering the binding of RNA polymerase to the promoter of a structural gene encoding a protein, or complementary binding of the nucleotide sequence to at least a part of the structural gene, thus typically reducing the quantity of the protein in the cell.

By "derivative" of mannose or xylose is meant any compound capable of being utilized by, binding to, being a substrate for, or a product of any protein involved, either directly or indirectly, in the metabolism of mannose or xylose. In the case of mannose, it will be appreciated that such derivatives include carbohydrates, such as glucose or galactose which may be subject to the actions of epimerases thereby yielding mannose or derivatives or precursors thereof. "Derivative" also includes mannose or xylose residues having one or more hydroxyl groups to which residues are covalently or ionically attached. Such attached residues include esters, ethers, amino groups, amido groups, phosphate groups, sulphate groups, carboxyl groups, carboxyalkyl groups, and combinations thereof. Mannose or xylose derivatives may also include mannose or xylose precursors, if the derivatizations are capable of being removed in such a way as to yield mannose or xylose.

The term "cell" within the context of the invention includes protoplasts, and the term "population of cells" includes a tissue, an organ or a portion thereof, a population of individual cells in or on a substrate, or a whole organism, for example, a plant.

The present invention also includes transformed cells which have been selected using the method of the invention, and such transformed cells which are plant cells, as well as plants, progeny or seeds derived from such cells. Plants which may be selected according to the invention include: fruits, including tomatoes, mangoes, peaches, apples, pears, strawberries, bananas, and melons; field crops such as canola, sunflower, tobacco, sugar beet, small grain cereals such as wheat, barley and rice, corn and cotton, and vegetables such as potato, carrot, lettuce, cabbage and onion.

The particularly preferred plants are sugar beet and corn.

Use of the present positive selection method in vivo is of particular relevance, for example, in connection with transformation performed on whole plants or on plant parts, in which the plants or parts comprise both transformed and non-transformed cells, since selection of the transformed cells is achieved without directly damaging the neighboring non-transformed cells. The transformed cells thus have a selective "advantage" compared to the non-transformed cells (e.g. the ability to form shoots), but the non-transformed cells do not suffer any severe disadvantage in the sense of being damaged or killed, as in the case with negative selection using antibiotics or herbicides.

The "selective advantage" possessed by the transformed cells may typically be a difference or advantage allowing the transformed cells to be identified by simple visual means, i.e. without the use of a separate assay to determine the presence of a marker gene.

A population of cells may be cultivated on or in a medium containing at least one compound which may be inactive and which is directly or indirectly activated in the transformed cells, the compound being inactive in non-transformed cells or less active in non-transformed cells than in transformed cells, such that the transformed cells are provided with a selective advantage allowing them to be selected from the cell population.

The population of cells may also be cultivated on or in a medium containing a compound which is made available for the transformed cells by expression or transcription of the nucleotide sequence, the compound not being available for the non-transformed cells or being less available for non-transformed cells, such that the transformed cells are provided with a selective advantage.

When a polypeptide encoded by the nucleotide sequence directly activates an inactive compound in the transformed cells, the non-transformed cells may endogenously contain or produce a certain amount of the said polypeptide which may typically be an enzyme. In such cases the "inactive compound" need not necessarily be completely inactive in the non-transformed cells, since it may be sufficient that the compound or nutrient is merely substantially less active in non-transformed cells than in transformed cells. In other words, a qualitative difference between the transformed cells and the non-transformed cells with regard to activation of the initially inactive compound may be sufficient for selection purposes. In such cases inhibitors or substrates which compete with the native enzymes may be added to the cells. Especially suitable are inhibitors activated by the native enzyme, resulting in self-catalyzed production of the active inhibitor to a level at which the native enzyme is substantially totally inhibited.

The cells may also be transformed with a co-introduced nucleotide sequence which may encode a permease or other transport factor which allows the compound to cross the cell membrane and enter the transformed cells or to cross another (organelle) membrane, so that "activation" of an inactive compound involves selective uptake of the compound by transformed cells, and uptake by non-transformed cells is not possible or takes place to a lesser extent. Instead of facilitating uptake of a compound into the cell, the co-introduced nucleotide sequence may alternatively direct its product to a compartment in which the inactive compound is located, for example, outside the plasma membrane or into the vacuole or the endoplasmic reticulum.

Where two nucleotide sequences are co-introduced into cells they may optionally be coupled to each other or otherwise introduced together in such a manner that the presence of one nucleotide sequence in the cell indicates the presence, or increased likelihood of the presence, of the other sequence in the cell. The two nucleotide sequences are thus typically, although not necessarily, part of the same genetic construct and may be introduced via the same vector.

Since it is necessary that the introduced nucleotide sequences are expressed in the transformed cells, a genetic construct containing the two nucleotide sequences will typically contain regulatory sequences enabling expression of the nucleotide sequences, e.g. known promoters and transcription terminators. Thus, the co-introduced nucleotide sequence will typically be associated with a promotor, which may be constitutive or regulatable.

The methods described herein may also be used when the two nucleotide sequences are introduced independently. This may be performed, for example, by using the same bacteria for incorporation of both genes and incorporating a relatively large number of copies of the desired nucleotide sequence into the cells, whereby the probability is relatively high that cells which are shown to express the co-introduced nucleotide sequence also will contain and express the desired nucleotide sequence. Independent introduction of two or more genes resulting in co-expression of the genes in the same cell is generally expected to have a low probability, and the improved selection frequencies obtained by the positive selection method are therefore expected be especially advantageous in such systems.

A compound used for selection purposes may in addition have both a positive and a negative effect. For example, mannose in sufficiently high concentrations is toxic to most plants, but in cells containing mannose metabolizing enzymes, the negative effect is eliminated and the cells further obtain the benefit of being able to use mannose as a carbohydrate source. In this case a single compound and a single gene together provide a combined positive and negative selection system, although such a system may also be established using two or more genes which together are responsible for inhibition of the negative effects of a compound and manifestation of the positive effects of the compound in the transformed cells.

In a further embodiment of the method, expression or transcription of the nucleotide sequence results in blockage of the metabolism of a compound supplied to the population of cells or blockage of the synthesis of a compound in the transformed cells, whereby the transformed cells can be identified or selected from the non-transformed cells.

In a still further embodiment of the method, the transformed cells may be selected using a combination of positive selection and negative selection, the nucleotide sequence in the transformed cells being co-introduced with a further nucleotide sequence coding for resistance to at least one member selected from the group consisting of toxins, antibiotics and herbicides, and the medium in or on which the cells are cultured comprising at least one member selected from the group consisting of toxins, antibiotics and herbicides to which the transformed cells are rendered resistant. It is preferred that the nucleotide sequence is co-introduced with at least two different selection genes.

It is preferred that the compound is mannose or xylose. As indicated above, the compound may however, be a mannose derivative, for example mannose 6 phosphate, or a xylose derivative such as a xylose phosphate, or a mannose or xylose precursor.

The cells may be transformed with any nucleotide sequence which it is desired to incorporate thereinto. Such a nucleotide sequence may encode genes providing for viral, fungal, bacterial or nematode resistance.

The cells may be transformed by a bacterium, such as an Agrobacterium species, which is sensitive to the compound so that selection of the transformed cells by the compound has the advantage of reducing the risk of post-transformation infection of the transformed cells by the bacteria. It will be appreciated that the cells may be transformed by any suitable known means including electroporation, micro-injection, use of the micro-projectile gun, and transformation with Ri and Ti plasmids. The transformed cells may, in suitable cases, be regenerated into whole plants in which the recombinant DNA is stably incorporated into the genome.

The protein is preferably an enzyme involved in mannose or xylose metabolism. Such enzymes include xyloisomerases and phosphomanno-isomerases such as mannose 6 phosphate isomerase and mannose 1 phosphate isomerase; phosphomanno mutase; mannose epimerases such as those which convert carbohydrates to mannose or mannose to carbohydrates such as glucose or galactose; phosphatases such as mannose 6 phosphatase and mannose 1 phosphatase, and permeases which are involved in the transport of mannose, or a derivative, or a precursor thereof into the cell.

The agent which reduces the toxicity of the compound to the cells is typically a glucose derivative such as methyl-3-O-glucose or phloridzin.

The present invention will be still further apparent from a consideration of the following text in conjunction with the accompanying drawings in which.

Figure 3:
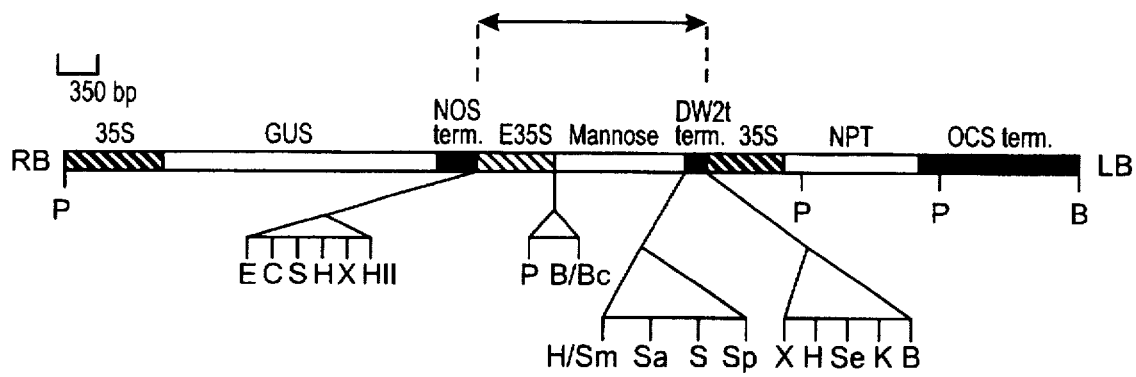
Figure 4:
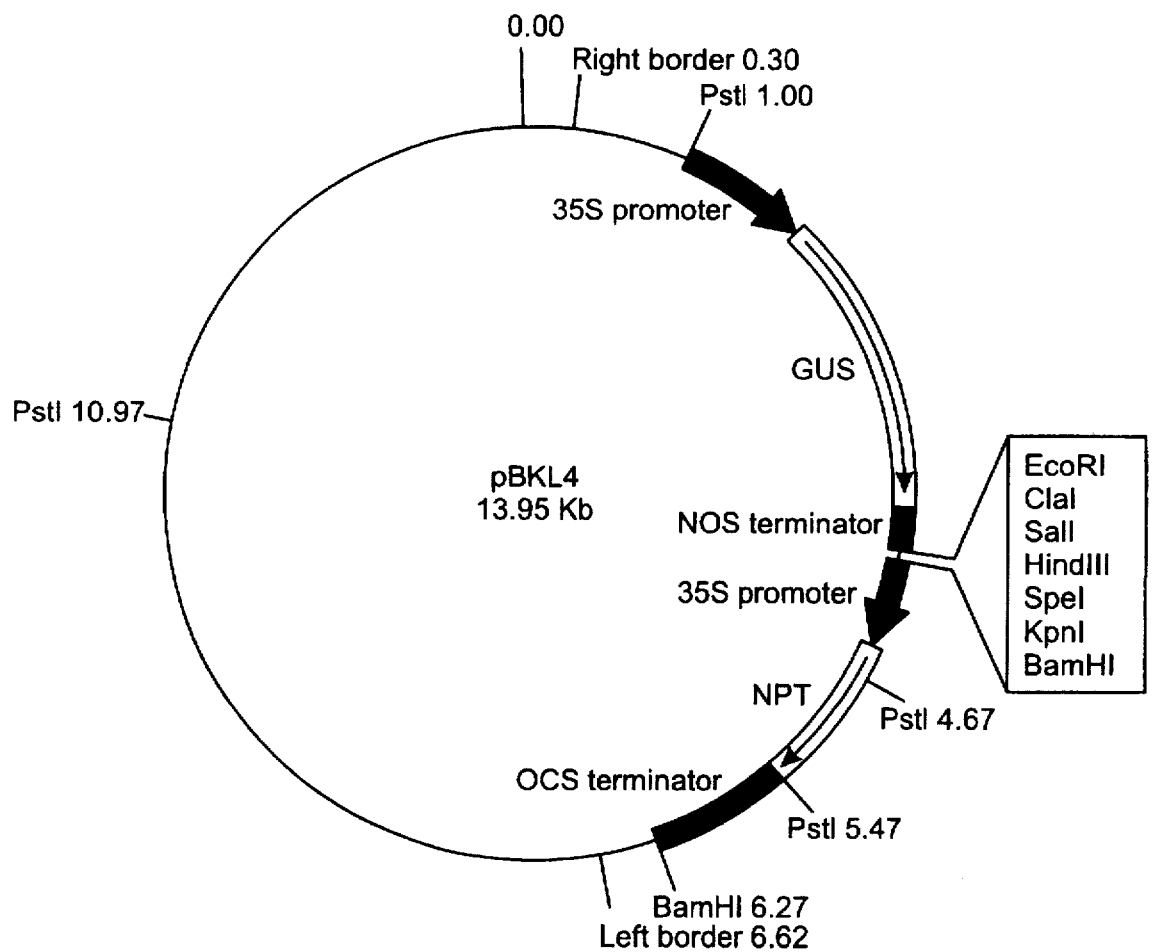

FIG. 3 shows the binary plasmid pBKL4 (Nielsen, K.K. et al. Mol. Plant Microbe Interact. 6 pp495–506 (1993));

FIG. 4 shows plasmid pBKL4 containing the man A gene inserted between the GUS Gene and the NPTII gene.

CONSTRUCTION OF THE BINARY PLASMID

P(BKL4-MANNOSE) CONTAINING, THE *E. COLI* PHOSPHOMANNOSE ISOMERASE CODING SEQUENCES

The *E. coli* phosphomannose isomerase (EC 5.3.2.8) gene originates from plasmid pGS63 (Miles, H. et al. Gene 32, pp41–48 (1984)) (FIG. 1), a construction derived from pBR322, in which the region between the unique PstI and HindIII sites has been replaced by a section of the *E. coli* chromosome bearing the structural gene (man A) for phosphomannose isomerase and a fragment of the adjacent gene for fumarase (fum A). pGS63 has therefore lost a portion of the β-lactamase gene and has to be selected on tetracycline.

Figure 1:
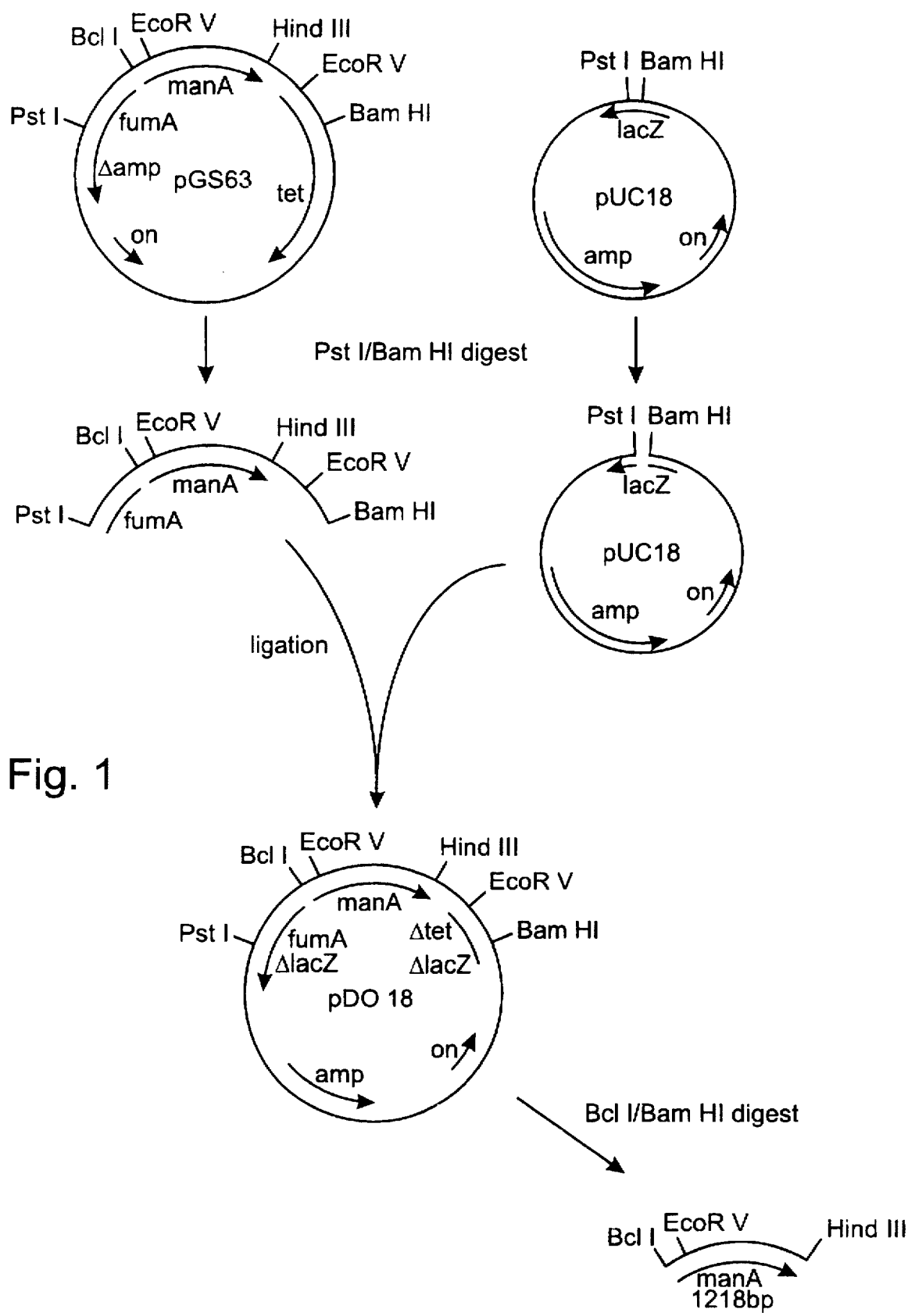
FIG. 1 shows the preparation of a BCl 1/HindIII restriction fragment comprising the coding region of the E. coli. phosphomannose isomerase.
Figure 2:
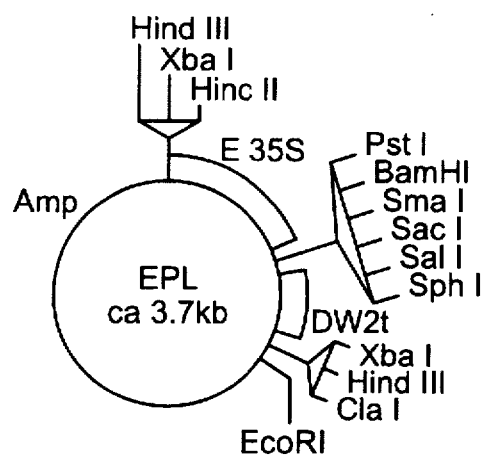
FIG. 2 shows plasmid EPL (Pietrzak, M. et al. Nucleic Acids Re.s 14 pp5857–5868 (1986))

The PstI/BamHI fragment (2466 bp) containing the entire PstI/HindIII chromosomal fragment and a 357 bp section of pBR322 was ligated into the multiple cloning site of pUC18 to form pDO18 (see FIG. 1).

pDO18 is digested with HindIII and the resultant recessed 3' termini are filled using Klenow polymerase. The open DO18 plasmid with the filled HindIII site (HindIII*) (See FIG. 1) is digested with BcII and the 1218 bp BcII-HindIII* fragment containing the coding region of phosphomannose isomerase is cloned into the plasmid pEnhanced-Peter-Linker (pEPL), which was first digested with SmaI and then with BamHI. The resultant plasmid is called p(EPL-mannose).

pEPL is constructed from pCaMVCN (Fromm et al. Proc. Natl. Acad. Sci. USA 82, p5824 (1985); Fromm et al. Nature 319, p791 (1986)) in which the CAT gene is removed by a PstI digestion. A small linker (linker: PstI-BamHI-BalI-PstI) is inserted into this plasmid PstI site, giving the plasmid called pLise(pL). pL is digested with HincII and BglII and the resultant fragment containing the 35S promoter and the NOS terminator is cloned into another pL plasmid digested with EcoRV and BglII. Both EcoRV and HincII are blunt ended sites. The resulting construct is called pEnhanced-Lise (pEL). pEL differs essentially from pCaMVCN in that it contains a variant 35S promoter with a tandem duplication of the 250 bP of the upstream sequence of the promoter. The variant 35S promoter has a transcriptional activity approximately ten times higher than the natural 35S promoter (Kay et al. Science 236, pp. 1299–1302 (1987)). pEL is digested with PstI and BglII, thereby removing the NOS terminator, and a CaMV terminator (DW2t) is inserted instead. Finally, a linker (PstI-BamHI-SmaI-SacI-SalI-SphI) is inserted into the PstI site situated between the enhanced 3e5S promoter and the CaMV terminator. This plasmid is called pEPL (see FIG. 2).

p(EPL-mannose) is digested with HindIII in order to isolate the fragment containing the entire enhanced 35S promoter, the coding region of *E. coli* phosphomannose isomerase and the CaMV terminator. The isolated fragment is cloned into the HindIII site of the binary vector pBKL4 (FIG. 4). The resulting plasmid is termed p(BKL-mannose). The HindIII site in pBKL4 is situated between a kanamycin resistance gene and the β-glucuronidase (GUS) gene (see FIG. 3). The mannose chimeric gene, the kanamycin resistant gene (NPT II) and the GUS gene each have a promoter and terminator. FIG. 4 shows the p(BKL-mannose) construction containing the chimeric phosphomannose isomerase gene inserted between the GUS and the NPTII gene of plasmid pBLK4.

The construct p(BKL-mannose) is isolated from *E. coli* and transformed into the *Agrobacterium tumefaciens* strain LBA4404 which contains the disarmed helper plasmid pAL4404 (Hoekema, et al. Nature, 303, pp. 179–180 (1983); Ooms et al. Plasmid 7, pp. 15–29 (1982)) by the freeze thaw methods (Holsters et al., Mol. Gen. Genet 163, 181–187 (1978)).

The sequence of the structural gene (man A) encoding phosphomannose isomerase has been published by Miles and Guest (Gene 32, 41–48 (1984)).

Axenic Stock Cultures.

Shoot cultures of *Solanum tuberosum* 'Saturna' 'Binge' or 'Dianella' are maintained as described by Linsmaier and Skoog (Physiol. Plant. 18: 100–127 (1965)), on an LS substrate (see below) supplemented with 2uM silver thiosulfate, the temperature being 25° C. and the cultures being subjected to cycles having 16h light/8h dark. The stock cultures are sub-cultured after 20–40 days. Leaves were removed from the shoots and cut into nodal segments (approx. 0.8 cm) each containing one node.

Inoculation of Potato Tissues.

Co-cultivation plates contain LS substrate (sucrose 30 g/l), agar (8 g/l), 2,4-dichlorophenoxyacetic acid (2.0 mg/l) and trans-zeatin (0.5 mg/l).

Shoots from approx. 40 day old shoot cultures (height approx. 5–6 cm) are cut into internodal segments (approx. 0.8 cm). The segments are placed into liquid LS-substrate (LS-medium) containing *Agrobacterium tumefaciens* transformed so that it contains a binary vector comprising genes which it is intended should be incorporated into the potato cells. Such genes include, for example, those encoding β-glucuronidase (GUS), the NPT II gene providing resistance to the antibiotic kanamycin and/or genes encoding proteins involved in mannose metabolism, for example mannose 6 phosphate isomerase, mannose epimerases, phosphomannomutases etc. (see below).

The Agrobacterium are cultured over-night in YMB-substrate (dipotasiumhydrogenphosphate (trihydrate) (0.66 g/l); magnesium sulphate (heptahydrate) (0.20 g/l); sodium chloride (0.10 g/l); mannitol (10.0 g/l); and yeast extract 0.40 g/l) containing appropriate antibiotics (corresponding to the resistance gene of the Agrobacterium strain) to an optical density at 660 nm (OD-660) of approx. 0.8. The suspension is then centrifuged and the cells resuspended in the LS-medium so that the OD-660 thereof is 0.5.

The above mentioned internodal segments are then incubated in the suspension of the resuspended Agrobacterium for about 30 minutes, and then the excess of bacteria is removed from the segments by blotting them onto sterile filter paper.

Co-cultivation of the Shoot Segments and Agrobacterium

The shoot segments are co-cultured with bacteria for 72 hours on filter paper on LS-substrate (as defined above) in petri-dishes covered with white paper tissues. This substrate is referred to hereafter as "co-cultivation substrate". The substrate and segments are covered with sterile filter papers, and the petri dishes are placed at 25° C. and subjected to cycles of 16h light/8h dark.

Washing Procedure

After 48 hours of co-cultivation, the shoot segments are transferred to LS-medium supplemented with 800 mg/l carbenicillin. The thus transferred segments are then gently shaken to dislodge or destroy adherent Agrobacteriwn.

Selection of Transformed Tissue

The thus washed segments are then transferred to LS-substrate (as above) except that the trans-zeatin concentration was 1 mg/l, and the substrate is supplemented with gibberellic acid (0.1 mg/l) and carbenicillin (800 mg/l), and optionally kanamycin sulphate (50 mg/l) and/or mannose (0–20 g/l) and/or sucrose (0–20 g/l). This substrate is referred to herafter as "selection/regeneration substrate".

The segments are sub-cultured onto fresh substrate at fortnightly intervals or as described below. Within 2 to 4 weeks, shoots developed from the segments and the formation of new shoots continues for about 3–4 months.

Rooting of Regenerated Shoots

The regenerated shoots are transferred to rooting substrate composed of LS-substrate supplemented with carbenicillin (500 mg/l).

Transfer or Regenerated Shoots to Soil

The newly rooted regenerated shoots (plants) (height approx. 2–3 cm) are transplanted from rooting substrate to soil and placed in a growth chamber at 21° C. having a 16 hour light/8 hour dark cycle and 200–400 uE/sqm/sec. When the plants are sufficiently well established they are transferred to a greenhouse, where they are grown until tubers develop and the upper part of the plants exhibit senescence.

Verification of the Genetic Identity of the Transformants

The transgenic genotypes of the regenerated shoot are verified:

(a) by performing NPTII assays as described by Radke et al (Theor. Appl. Genet. 75, 685–694 (1988)); or (b) by performing a GUS assay on the enzyme expressed by the co-introduced β-glucuronidase gene according to Hodal et al. (Plant. Sci. 87, 115–122 (1992)); or (c) by assaying for the expression of the mRNA of the introduced gene encoding an enzyme, for example phosphomannose isomerase, involved in mannose metabolism, or by measuring the activity of the enzyme.

EXAMPLE 1

Regenerated plants are produced as described above, except that the shoot segments are not co-cultured with bacteria and the washing procedure consequential thereon is omitted. The number of regenerated shoots is determined up to the 40th day from the start of experiment. Table 1 shows the inhibition by mannose of the regeneration of shoots from potato stem segments which had not been transformed with Agrobacterium. It can be seen from Table 1 that mannose effectively inhibits regeneration of such shoots, and that sucrose promotes such regeneration. In general, mannose cannot be used as a carbohydrate source in most plant species. When mannose is added to plants it is metabolized and mannose 6-phosphate accumulates. Mannose 6-phosphate can be converted to fructose 6 phosphate by mannose 6 phosphate isomerase, the amount converted being dependent up on the activity of the isomerase. Such fructose 6 phosphate may be utilized by plants, but in principal high levels of mannose (whether or not an alternative carbohydrate source is available) are toxic to plants. Thus, as can be seen, from Table 1, shoot formation is totally inhibited when the mannose concentration is 5–10 g/l, irrespective of the availability of sucrose, even when that is present in high concentrations.

TABLE 1

Inhibition by mannose of the regeneration of shoots from non-transformed potato stem segments.

| Concn (g/l) sucrose | Concn (g/l) mannose | Regenerated shoots/explant (%) |
|---|---|---|
| 0 | 0 | 0 |
| 0 | 5 | 0 |
| 0 | 10 | 0 |
| 0 | 20 | 0 |
| 10 | 0 | 50 |
| 10 | 5 | 3 |
| 10 | 10 | 0 |
| 10 | 20 | 0 |
| 20 | 0 | 53 |
| 20 | 5 | 0 |
| 20 | 10 | 0 |
| 20 | 20 | 0 |

EXAMPLE 2

Regenerated plants are produced as described above. The Agrobacterium with which the shoot segments are co-incubated are transformed with construct p(BKL-mannose) which is obtained as described above, so that the bacteria harbour a vector comprising the genes encoding GUS and mannose 6 phosphate isomerase.

Transgenic (GUS+) shoots are selected on the basis of their ability to metabolize mannose in the presence of an agent (methyl-3-O-glucose) which reduces the toxicity to the shoots of the mannose. Shoots which are GUS+ are selected on the basis of their ability to grow in the presence of mannose at a concentration of about 5 g/l.

Control experiments were also performed in which the Agrobacterium which were used to transform the shoot segments harbored a vector similar to p(BKL-mannose) except that it lacked the gene encoding mannose 6 phosphate isomerase. No GUS+ transformants were obtained when the regenerated transformed shoots were grown in the presence of mannose at 5 g/l and sucrose at 20 g/l.

EXAMPLE 3

A further experiment is performed in which the Agrobacterium which are used to transform the shoot segments harbour a vector similar to p(BKL-mannose) except that it lacks the gene encoding mannose 6 phosphate isomerase. Such a vector comprises the gene encoding NPT II which is capable of rendering cells transformed therewith resistant to kanamycin. Accordingly, GUS+ transformants are selected on the basis of their resistance to kanamycin present at a concentration of 50 mg/l. In this latter selection, a lower proportion than in Example 2 of the selected cells are GUS+.

EXAMPLE 4

Example 3 is repeated, except that the Agrobacterium are transformed with p(BKL-mannose) and the GUS+ transformants are selected on the basis of their ability to grow on Kanamycin (50 mg/ml). In this case a lower proportion than in Example 3 of the selected shoots are GUS+.

EXAMPLE 5

The standard leaf disc procedure for tobacco as described in Example 13 of PCT/92/00252 is performed, except that inoculation with Agrobacterium and the co-cultivation step are omitted. Benzyladenine (1 mg/l) is used as cytokinin and the carbohydrate content is as indicated below. The number of regenerated shoots from each leaf disc are registered after 21 days.

Table 2 shows that D-xylose does not inhibit shoot regeneration when sucrose is present and in addition that D-xylose is not utilized as a carbohydrate source. D-xylulose is a good carbohydrate source during shoot regeneration.

TABLE 2

Test of the ability of D-xylose and D-xylulose to function as carbohydrate sources during shoot regeneration from tobacco leaf discs.

| Xylose g/l | Sucrose g/l | Xylulose g/l | Number of regenerated shoots each leaf disc |
|---|---|---|---|
| 0 | 0 | 0 | 0 |
| 10 | 0 | 0 | 0 |
| 10 | 10 | 0 | 4.3 |
| 0 | 10 | 0 | 2.3 |
| 0 | 0 | 10 | 4.1 |
| 0 | 10 | 10 | 11.7 |

Xylose can be converted to xylulose by xylose isomerase. Accordingly, a functional xylose isomerase gene and a further structural gene under control of appropriate promoters and terminators, are introduced into plants, or parts or cells thereof, and the transformed plants, parts of cells thereof are selected on the basis of their ability to metabolism xylose as a carbohydrate source.

EXAMPLE 6

Explants are produced and treated as described above under "selection of transformed tissue", except that the selection/regeneration substrate was not supplemented with kanamycin or carbenicillin, and that plant tissue is not transformed. Thus the only subcultivation step is when the explants are transferred from the co-cultivation substrate to the selection/regeneration substrate which is supplemented with xylose at the concentrations indicated below. The number of regenerated shoots is recorded after 12 weeks.

TABLE 3

The ability of D-xylose to function as a carbohydrate source during shoot regeneration from potato stem segments.

| Xylose g/l | Sucrose g/l | Number of regenerated shoots each stem segment |
|---|---|---|
| 0 | 0 | 0 |
| 5 | 0 | 0 |
| 10 | 0 | 0 |
| 20 | 0 | 0 |
| 0 | 10 | 6 |
| 5 | 10 | 3 |
| 10 | 10 | 0 |
| 20 | 10 | 0 |

Table 3 shows that D-xylose (compared to D-mannose) is a weak inhibitor of shoot regeneration when sucrose is present and in addition D-xylose does not function as a carbohydrate source in plants which are non-transgenic in respect of a xylose metabolizing enzyme or protein. Moreover, D-xylulose (5 g/l) added to substrates in the absence of sucrose enabled the regeneration of 2.2 shoots per explant after 9 weeks.

EXAMPLE 7

Example 5 is repeated except that the selection/regeneration substrate is supplemented with methyl-3-O-glucose (MOG) at the concentrations indicated in Table 4. The percentage of live explants is registered after 8 weeks.

Table 4 shows that co-treatment with MOG inhibits the toxic effects of mannose on sensitive plant tissues. Because mannose is toxic in concentrations which are optimal for compounds which function as carbohydrate sources, the addition of MOG makes it possible to supplement the substrate with optimal carbohydrate concentrations in the form of mannose. This makes it possible to utilize mannose as a positive selection agent, in the absence of other carbohydrate sources.

TABLE 4

Inhibition of the toxicity of mannose by co-treatment with methyl-3-O-glucose (MOG).

| Mannose (g/l) | 0 | 5 | 10 | 0 | 5 | 10 |
|---|---|---|---|---|---|---|
| Sucrose (g/l) | 0 | 0 | 0 | 10 | 10 | 10 |
| MOG (g/l) | | | | | | |
| 0 | 71 | 4 | 0 | 100 | 1 | 4 |
| 5 | 13 | 54 | 0 | 100 | 100 | 5 |
| 10 | 47 | 82 | 9 | 100 | 100 | 41 |
| 20 | 50 | 98 | 88 | 100 | 100 | 100 |

EXAMPLE 8

Example 7 is repeated, except that the regeneration/selection substrate contains mannose (15g/l), methyl-3-O-glucose in the concentrations indicated in Table 5, and does not contain sucrose. The transformed plant material is transgenic for the mannose 6 phosphate isomerase gene. After 21 days the selected shoots are harvested. All harvested shoots are assayed for the expression the co-introduced β-glucuronidase gene and the total number (from 2 harvests) of transgenic β-glucuronidase expressing (GUS+) shoots per explants is calculated as is the fraction of the β-glucuronidase expressing (GUS+) shoots among the total number of shoots selected (Table 5.).

Table 5 shows that when mannose is added together with methyl-3-O-glucose, selection of transgenic shoots is possible even at high concentrations of mannose, in the absence of other carbohydrate sources.

TABLE 5

The effect of methyl-3-O-glucose on the selection of transgenic shoots on mannose containing substrates without sucrose.

| Mannose (g/l) | 15 | 15 | 15 | 15 | 15 |
|---|---|---|---|---|---|
| MOG (g/l) | 0 | 2.5 | 5.0 | 10 | 15 |
| GUS+ shoots/explant | 0 | 0.2 | 1.0 | 0.5 | 0.6 |
| GUS+ shoots/ sel. shoots (%) | 0 | 57 | 81 | 89 | 53 |

EXAMPLE 9

Example 8 is repeated except that MOG is substituted by phloridzin. Table 6 shows that when mannose is added together with phloridzin selection of 100% transgenic shoots is possible at high concentrations of mannose in the absence of other carbohydrate sources. This is an example of how cross feeding and the production of escapers can be minimized by the addition of a carbohydrate transport inhibitor.

TABLE 6

| | 0.5 g/l Phloridzin | | | |
|---|---|---|---|---|
| | GUS+ Shoots/Sel. Shoots | | GUS+ Shoots/Expl. | |
| g/l Mannose | +Sucrose | +Sucrose | +Sucrose | +Sucrose |
| 5.0 | 94.0% | 100.0% | 1.2 | 0.08 |
| 7.5 | 88.0% | 78.5% | 0.5 | 0.5 |
| 10.0 | 100.0% | 95% | 0.5 | 0.5 |
| 12.5 | 100% | — | 0.03 | 0.0 |
| 15.0 | 100% | — | 0.03 | 0.0 |

EXAMPLE 10

Table 7 indicates that compounds other than mannose may be used as selection agents in transgenic plant tissue which comprises, inter alia, the mannose 6-phosphate isomerasse gene from E. coli.

TABLE 7

No. of regenerated shoots per explant selected by compounds in addition to mannose.
Number of regenerated shoots per explant

| | Genotype | |
|---|---|---|
| Compound | Wild type | M-6-P-isomerase |
| D-mannose | 0 | 1.1 |
| D-mannosamine | 0 | 0.8 |
| D-mannose-6-phosphate | 0 | 0.7 |

EXAMPLE 11

Sugar beet is transformed by the so-called cot-pet method as described in PCT Patent Application No. PCT/DK92/00108 wherein cotyledons including the petiole are used as explants. Seedlings are derived from seeds germinated and grown for 4–7 weeks at 12° C. in a 16h day/8h night regime. Cotyledons are excised 2–3mm below the node, tawn apart and cultured either in the dark or in light and in the presence or absence of xylose. Table 8 shows that xylose is utilized as a carbohydrate source by sugar beet in the presence of light but not in the dark indicating that xylose based positive selection of sugar beet which are transgenic inter alia for the xylose isomerase gene should be carried out in the dark.

TABLE 8

Examination of the effect of D-xylose in sugarbeets in combination with sucrose with and without light

| D-xylose (g/l) | Sucrose (g/l) | % expl. with shoots | weight (wet) (g) | Green (%) |
|---|---|---|---|---|
| Results after 3 weeds (light) | | | | |
| 0 | 10 | 98 | 7.41 | 100 |
| 0 | 0 | 13 | 0.64 | 60 |
| 10 | 0 | 90 | 1.53 | 90 |
| 10 | 10 | 97 | 5.47 | 100 |
| Results after 2 weeks in darkness and 1 week in light | | | | |
| 0 | 10 | 50 | 1.38 | 97 |
| 0 | 0 | 0 | 0.36 | 47 |
| 10 | 0 | 13 | 0.37 | 77 |
| 10 | 10 | 80 | 0.89 | 97 |

EXAMPLE 12

Explants transgenic, inter alia, for the mannose 6 phosphate isomerase gene are produced, and the selection/regeneration substrate is supplemented with mannose and sucrose as indicated in Table 9. The number of regenerated shoots is registered after 11 weeks. Table 9 shows the number of regenerated shoots on substrates containing methyl-3-O-glucose as a percentage of the number of shoots regenerated on substrates without mannose and methyl-3-O-glucose.

TABLE 9

| | | Methyl-3-O-glucose (g/l) | | | |
|---|---|---|---|---|---|
| Mannose | Sucrose | Wild type | | Man-6-P-isomerase | |
| g/l | g/l | 2.5 | 5.0 | 2.5 | 5.0 |
| 0 | 0 | 0 | 0 | 0 | 0 |
| 5 | 0 | 0 | 0 | 7 | 0 |
| 10 | 0 | 0 | 0 | 64 | 28 |
| 20 | 0 | 0 | 0 | 107 | 128 |
| 0 | 10 | 53 | 17 | 0 | 0 |
| 5 | 10 | 6 | 41 | 64 | 64 |
| 10 | 10 | 0 | 0 | 86 | 36 |
| 20 | 10 | 0 | 0 | 200 | 86 |

Regeneration of shoots on substrate containing sucrose (10 g/l), no mannose and no methyl-3-O-glucose:
Transgenic tissue: 1.4 shoots/explant
Wild type tissue: 1.7 shoots/explant It will appreciated that the present invention is not limited to the above identified Examples. For example, tissue specific expression of a gene encoding an enzyme involved in mannose or xylose metabolism, or the metabolism of a mannose or xylose derivative or a mannose or xylose pre-cursor may be used to control developmental regulation of such tissues upon exposure thereof to the substrate of modulator of the said enzyme. Moreover, mannose or xylose (including derivatives or precursors thereof) may be used as a selective herbicide to selectively advantage crops which have been transformed to include genes encoding proteins involved in the metabolism of such xylose or mannose or their precursors or derivatives.

It will also be appreciated that use of the method according to the invention may yield:

i) eukaryotic organisms having in general or in some tissues/cell types decreased levels of fructose 6 phosphate, or derivatives thereof, by virtue of introduction of a gene encoding, for example, phosphomannose isomerase;

ii) eukaryotic organisms having in general or in some tissues/cell types increased levels of mannose 6 phosphate, or derivatives thereof, by virtue of introduction of a gene encoding, for example, phosphomannose isomerase;

iii) eukaryotic organisms having in all or some cell types increased phosphomannoisomerase activity by virtue of the introduction of a gene encoding phosphomannoisomerase into the cells thereof.

We claim:

1. A method for selecting genetically transformed plant cells from a population of cells comprising:

a) introducing into plant cells a desired nucleotide sequence and a co-introduced nucleotide sequence to obtain transformed plant cells;

b) supplying to a population of plant cells including the transformed cells and non-transformed cells a compound selected from the group consisting of mannose and a derivative or precursor of mannose, wherein said transformed cells have a competitive advantage over the non-transformed plant cells in the population due to the expression or transcription of the co-introduced nucleotide sequence in the transformed cells; and c) selecting the transformed plant cells based on said competitive advantage wherein said co-introduced nucleotide sequence is a gene encoding an enzyme involved in mannose metabolism selected from the group comprising a phosphomanno isomerase, a phosphomanno mutase, a mannose epimerase, a phosphatase, and a permease.

2. The method of claim 1 wherein the compound is mannose.

3. The method of claim 1 wherein the co-introduced nucleotide sequence encodes mannose-6-phosphate isomerase.

4. The method of claim 1 wherein the compound is mannose and the co-introduced nucleotide sequence encodes mannose-6-phosphate isomerase.

5. The method according to claim 1 wherein the compound is mannose-6-phosphate or D-mannoseamine.

6. The method of claim 1 wherein the co-introduced nucleotide sequence encodes mannose-6-phosphatase.

7. The method of claim 1 wherein the cells have been transformed by a bacterium which is sensitive to the compound.

8. The method of claim 1 further comprising negative selection including, transforming cells with a further nucleotide sequence coding for resistance to a toxin, antibiotic, or herbicide; supplying to the population of cells a toxin, antibiotic or herbicide to which the transformed cells are rendered resistant; and selecting transformed cells.

9. The method of claim 1 wherein the desired nucleotide sequence and the co-introduced nucleotide sequence are introduced with a selection gene that differs from the co-introduced nucleotide sequence.

10. The method of claim 1 further comprising supplying a toxicity reducing agent with the compound to the population of cells.

11. The method of claim 10 wherein the toxicity reducing agent is methyl-3-O-glucose or phloridzin.

12. Transformed cells selected according to the method of claim 1.

13. Transformed cells according to claim 12 wherein said cells are potato, sugar beet or corn cells.

14. Genetically transformed corn cells comprising, an introduced desired nucleotide sequence and a co-introduced nucleotide sequence, wherein the expression or transcription of said co-introduced nucleotide sequence gives the transformed cells a competitive advantage over non-transformed cells when both transformed and non-transformed cells in a population of cells are supplied with a mannose compound and said transformed cells are selected based on said competitive advantage, wherein the co-introduced nucleotide sequence codes for a phosphosugar isomerase.

15. The genetically transformed cells of claim 14 wherein the co-introduced nucleotide sequence codes for mannose6-phosphate isomerase.

16. Plants derived from the genetically transformed corn cells of claim 14.

17. Genetically transformed plant cells comprising an introduced nucleotide sequence and a co-introduced nucleotide sequence wherein the expression or transcription of the co-introduced nucleotide sequence gives the transformed cells a competitive advantage over non-transformed cells when both transformed and non-transformed cells in a population of cells are supplied with a compound and said transformed cells are selected based on said competitive advantage, wherein the co-introduced nucleotide sequence is a gene encoding an enzyme involved in mannose metabolism selected from the group comprising a phosphomanno isomerase, a phosphomanno mutase, a mannose epimerase, a phosphatase, and a permease.

18. The genetically transformed plant cells according to claim 17 wherein said plant cells are sugar beet or potato cells.

* * * * *